United States Patent
Ross et al.

(10) Patent No.: US 8,080,144 B2
(45) Date of Patent: Dec. 20, 2011

(54) GRADIENT ELUTION ELECTROPHORESIS

(75) Inventors: David J. Ross, Silver Spring, MD (US); Jonathan G. Shackman, Philadelphia, PA (US)

(73) Assignee: The United States of America as represented by the Secretary of Commerce, The National Institute of Standards and Technology, Washington, DC (US)

( * ) Notice: Subject to any disclaimer, the term of this patent is extended or adjusted under 35 U.S.C. 154(b) by 826 days.

(21) Appl. No.: 11/866,589

(22) Filed: Oct. 3, 2007

(65) Prior Publication Data
US 2010/0155241 A1    Jun. 24, 2010

(51) Int. Cl.
*G01N 27/447* (2006.01)
(52) U.S. Cl. .................. 204/451; 204/450; 204/549
(58) Field of Classification Search .......... 204/601–605, 204/451–455, 549
See application file for complete search history.

(56) References Cited

U.S. PATENT DOCUMENTS

| | | | |
|---|---|---|---|
| 3,705,845 A | 12/1972 | Everaerts | |
| 3,869,365 A | 3/1975 | Sunden | |
| 4,897,169 A * | 1/1990 | Bier et al. | 204/548 |
| 5,151,164 A * | 9/1992 | Blanchard et al. | 204/451 |
| 5,302,264 A * | 4/1994 | Welch et al. | 204/452 |
| 5,429,728 A | 7/1995 | Gordon | |
| 5,482,608 A | 1/1996 | Keely et al. | |

OTHER PUBLICATIONS

CAPLUS abstract for Reijenga et al. "Effect of electroosmosis on detection in isotachophoresis," Journal of Chromatography (1983), 260(2), 241-54.*

Ryslavy et al. "Electroomostic source of hydrodynamic flow for analytical isotachophoresis," Chemicke Listy (1978), 72 (6), 50 646-50.*

* cited by examiner

*Primary Examiner* — Alex Noguerola
(74) *Attorney, Agent, or Firm* — Butzel Long (57) ABSTRACT

A method for performing electrophoretic separation of ionic compounds which involves varying a bulk fluid flow though a separation path into which ionic species are continuously introduced and separated. The method can also include the introduction of a leading electrolyte into the separation path to form an ionic interface with the sample and an optional terminating electrolyte to enrich ionic species for higher detection resolution.

24 Claims, 6 Drawing Sheets

GRADIENT ELUTION ELECTROPHORESIS

TECHNICAL FIELD

The present invention relates in general to electrophoretic separations, both in capillaries and in microfluidic channels, in order to preconcentrate, separate and/or purify compounds from a sample mixture. More particularly the present invention relates to the combination of electrophoresis in the presence of a variable hydrodynamic flow with continuous introduction of sample. Further the present invention relates to microfluidic devices for conducting trace analysis which have small total footprint areas.

BACKGROUND ART

Electrophoresis is a well known analytical method for separation of ionic compounds (analytes) in a sample mixture through use of an applied voltage. The voltage is applied to either end of a separation path (U-tube, gel, capillary, microfluidic channel, etc.), and the analytes are thereby caused to move along the separation path. The separation mechanism is based mainly on differences in analytes' size and charge, although other factors can be exploited such as shape, density, affinity, etc. Early electrophoresis work utilized continuous sample introduction into a relatively large glass U-tube across which a voltage was applied; analytes were detected in free solution as discrete boundaries throughout the tube. Electrophoresis was then applied to hydrated gel supports (e.g., polyacrylamide gel electrophoresis, PAGE) and later to micron diameter capillary tubes (i.e., capillary electrophoresis or CE). Typically, CE utilizes a discrete sample injection into the capillary in the presence of buffer electrolytes where analytes are separated into discrete zones along the separation path; this mode is termed capillary zone electrophoresis (CZE). A fixed detector is placed near the capillary outlet, past which analytes of highest mobility migrate first followed by species of slower mobility; individual analytes are typically detected as bands or peaks. For example, with a negative voltage applied to the capillary inlet, positively charged analytes will be detected first, followed by neutral species, and finally species exhibiting a negative charge. The detector response can then be correlated to analyte migration speed and, through the use of standard mixtures, be used to identify and/or quantify analytes.

An alternative mode of CE utilizes a discontinuous buffer system formed by using leading and terminating electrolytes (LE and TE, respectively) which define the boundaries between which the analyte ions are compressed into adjacent zones; this mode is termed isotachophoresis (ITP), referring to the uniform velocity of the electrophoresis (iso=same and tacho=speed). The discontinuous electrolytes are associated with a discontinuous electric field across the ion zones, with the lowest field in the LE zone and the highest in the TE zone. Sharp boundaries exist between each adjacent zone. In conventional capillary ITP (cITP), a sample mixture is injected into a capillary filled with LE. Either TE is added to the sample or the sample reservoir is replaced following injection with a reservoir containing TE. Under electrophoresis conditions the sample components begin to separate into individual zones. Should an analyte begin to enter the LE zone (or next fastest analyte), it experiences a drop in field and lower velocity, hence returning it to its own zone. If the analyte enters the TE zone (or next slowest analyte), it experiences a higher electric field and higher velocity, again returning it to its own zone. These counter balancing forces lead to a steady-state of analyte concentrations in their respective zones. The concentration of analyte ($C_A$) in the zone is fixed based upon the Kohlrausch regulating function of the LE concentration ($C_{LE}$):

$$C_A = C_{LE} \frac{\mu_A(\mu_{LE} + \mu_{CE})}{\mu_{LE}(\mu_A + \mu_{CE})}$$

where $\mu_A$, $\mu_{LE}$, and $\mu_{CE}$ are the electrophoretic mobilities of the analyte, LE, and counter ion electrolyte in the LE solution, respectively. The above shows that as the mobility of the analyte approaches that of the LE, they will have equivalent concentrations. When high concentrations of LE are used, dilute analyte samples become highly concentrated. For relatively high analyte concentration, the upper bound on the focused analyte zone given by the Kohlrausch regulating function is quickly reached, and the length of the zone will increase as additional analyte is injected. The entire 'train' of LE, analyte(s), and TE all move at a uniform velocity. Commonly conductivity detection is employed and a 'staircase' output is observed, with each rise in conductance indicating a zone boundary and a plateau indicating the zone width. When using other on-line detectors, such as single response optical detection (e.g., fixed wavelength absorbance or fluorescence), differentiation of the continuous zones becomes difficult. In this case, non-detectable 'spacer' ions can be introduced, either as discrete spacers between two zones or as a continuum of electrophoretic mobilities, which can be realized through ampholytic mixtures.

At very low analyte concentration, the analytes are focused on the boundary between the LE and TE and form narrow, Gaussian peaks with a maximum concentration much lower than that of the LE. In this regime of operation with cITP, all of the analytes are focused at the same boundary, and there is no resolution of analytes. Consequently, concentration and resolution of trace analytes with prior art ITP methods are typically done in two steps in a technique known as transient ITP. Another approach that has been implemented in prior art ITP methods is to use one or more species of spacer electrolytes with mobilities that lie between those of the analytes of interest. Analytes are then focused at the interfaces between the LE, TE, and spacer electrolytes and can be well resolved. An additional approach is the use of a large number of spacer electrolytes with mobilities that form a nearly continuous range, such as an isoelectric focusing ampholyte mixture. With this approach, analytes with a continuous range of mobilities can be concentrated and focused.

The two primary electromotive forces in electrophoresis in a confined separation medium (i.e., tubular, capillary, or microfluidic channel) are analyte electrophoretic mobility and electroosmotic flow (EOF). EOF arises when a surface charge is present along the separation column; in glass-based separations with solutions above pH of approximately 2 the surface silanol groups exhibit net negative charges. Positively charged ions in the solution media (typically a buffered electrolyte solution) are drawn towards the negative surface forming an electrical double layer which can be mobilized axially under an applied voltage along the length the separation media. The mobile cations additionally cause movement of the bulk solution through viscous drag, referred to as EOF.

There are two primary disadvantages to the common method of performing cITP. First, the method requires an injection to load the mixture to be analyzed into the capillary as a minimally wide plug between the TE and LE. Second, long channels are required to produce high enrichment factors for dilute solutions or to produce high-resolution separations. Both of these disadvantages increase the space required to implement ITP in a microfluidic chip format. Although long separation channels can be fit into a small area on a microfluidic chip using a serpentine pattern, every turn in the path of the separation channel degrades the separation resolution. Consequently, microchip ITP still generally gives lower resolution separations than can be achieved with conventional capillary-based ITP.

Two sample loading techniques are in general use for CE: electrokinetic and hydrodynamic injections. The former relies upon electrophoresis to introduce the sample. The inlet is placed in the mixture media to be analyzed, a voltage is applied for a finite time, and the inlet is then placed in a blank solution containing only the background electrolytes. This method introduces preferential injection bias, as those analytes of highest mobility are injected to a greater extent than those of lower mobility. For example, when a negative voltage is applied to the inlet, positive species are injected both by electrophoresis and EOF, while neutral compounds are mobilized solely by EOF and negative species are pulled away from the inlet by electrophoresis while still being injected by EOF. This has additional disadvantageous consequences in ITP, as the slowest analytes will have the lowest enrichment based on the Kohlrausch regulating function.

Hydrodynamic injections can be accomplished similarly to electrokinetic methods by using a pressure differential across the separation column, as opposed to an electrical differential. Most commonly, this is employed using either a sample vial elevated relative to the column outlet (gravity fed) or by using a pump. While eliminating electrical injection bias, hydrodynamic injections suffer from possible sample injection plug broadening due to the laminar flow profile induced by the pressure differential, ultimately leading to analyte zone broadening and a loss in separation efficiency. Additionally, hydrodynamic injections are much more difficult to implement in a microfluidic format, either necessitating off-chip injection equipment or complicated fabrication procedures, as the gravity fed method of injection is not readily available.

There are many examples in the prior art of the use of bulk flow in conjunction with electrophoresis for enhanced resolution or reduced analysis times. The most common example is the use of the native, unmodified EOF of the silica capillary to induce a bulk flow in the direction opposite to the direction of migration of anionic analytes. The time required for the migration of analytes through the length of the separation capillary and the resolution of the separation are thus increased. In addition, there are many examples of the use of coatings or external electric fields to vary the EOF of silica capillaries so that the bulk flow is set to the value desired for a given separation problem.

In addition to controlling bulk flow through modifications of the EOF, pressure-driven flow has also been used in conjunction with EOF as a means of better regulating bulk flow during electrophoresis. In this manner, the bulk flow rate can be decoupled from the electrical characteristics of the system and employed in a way to generate a constant, bulk flow for CE using discrete injections. U.S. Pat. Nos. 5,429,728 and 5,482,608 are illustrative of the method.

Additionally, counter flow has been used in ITP in order to increase residence time of analytes on column to increase enrichment and resolution or as a step to remove LE prior to performing ITP coupled to CZE. U.S. Pat. Nos. 3,705,845 and 3,869,365 are illustrative of the method.

DISCLOSURE OF THE INVENTION

According to various features, characteristics and embodiments of the present invention which will become apparent as the description thereof proceeds, the present invention provides a method for performing electrophoretic separation of compounds which involves:

a) providing a separation path along which compounds are electrophoretically separated;

b) providing a sample containing the compounds to be separated in fluid contact with the separation path;

c) applying a voltage along the length of the separation path to drive electrokinetic motion of the compounds through the separation path; and d) varying a bulk fluid flow through the separation path.

According to one embodiment, leading electrolytes can be introduced into the separation path to form an ionic interface with the sample.

The present invention further provides an apparatus for performing electrophoretic separation of ionic compounds which comprises:

a sample reservoir containing a sample solution including compounds to be separated;

a separation buffer reservoir containing a buffer solution;

a separation path that connects the sample reservoir to the separation buffer reservoir;

a means for applying a voltage along the separation path; and a means for varying a bulk flow rate of fluid through the separation path over time.

BRIEF DESCRIPTION OF DRAWINGS

The present invention will be described with reference to the attached drawings which are given as non-limiting examples only, in which.

BEST MODE FOR CARRYING OUT THE INVENTION

The present invention incorporates a process for coupling continuous sample introduction with a variable hydrodynamic bulk flow for electrophoretic separations in a capillary, microfluidic channel, or other separation column. By changing the bulk flow velocity over time during the separation, analytes are sequentially eluted onto the separation column from the sample where they can individually be detected as zone boundaries. The present invention further provides a method for the enrichment and separation of the constituents of a sample mixture, which enrichment method can be used in conjunction with the process for coupling continuous sample introduction with a variable hydrodynamic bulk flow for electrophoretic separations in a capillary, microfluidic channel, or other separation columns.

Figure 1A:
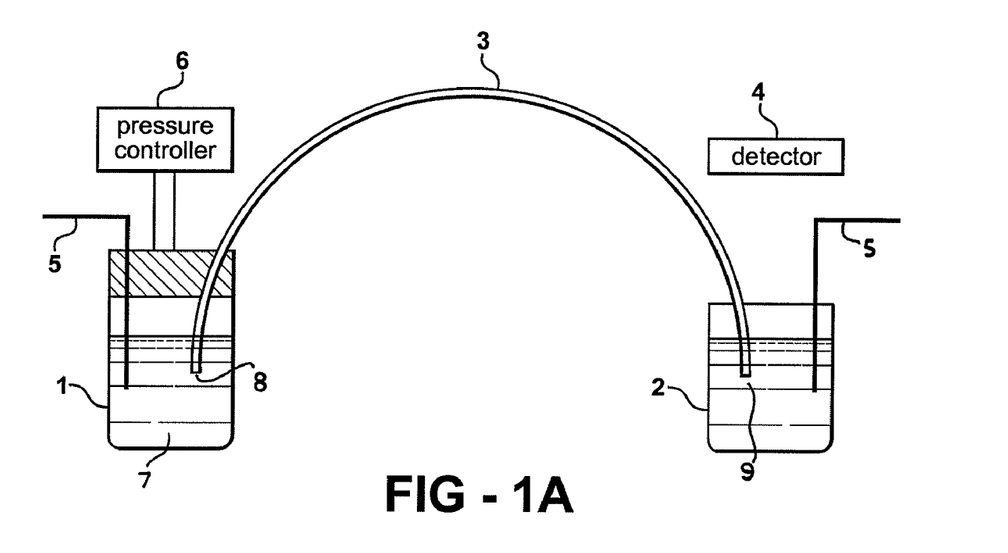
FIG. 1a is a schematic drawing of a capillary system that can be used according to one embodiment of the present invention.
Figure 1B:
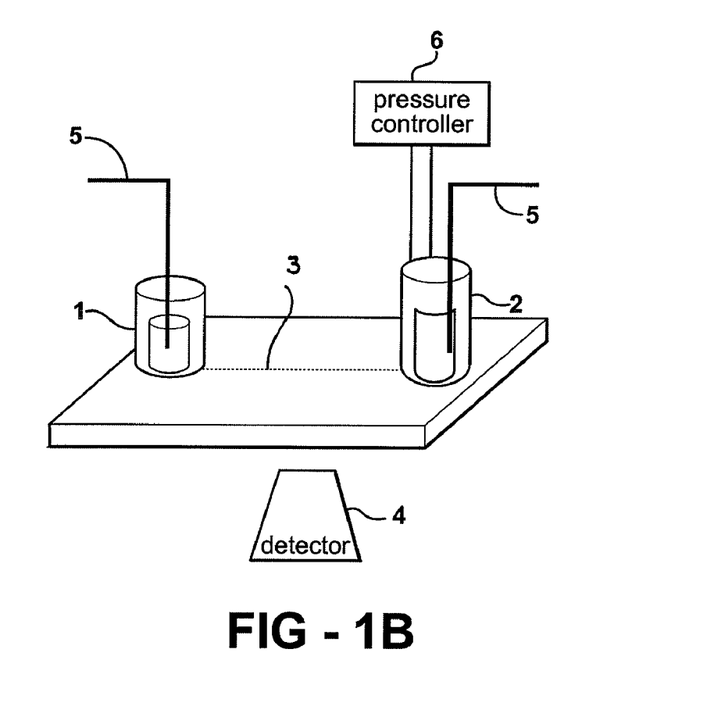
FIG. 1b is a schematic drawing of a microfluidic system that can be used according to one embodiment of the present invention.

The method can be applied to a capillary or microfluidic system. In this regard FIG. 1a is a schematic drawing of a capillary system that can be used according to one embodiment of the present invention and FIG. 1b is a schematic drawing of a microfluidic system that can be used according to one embodiment of the present invention.

A typical apparatus includes a sample reservoir 1 containing a sample 7, a separation buffer reservoir 2, a separation column 3 having an inlet end 8 and an outlet end 9 that connects the two reservoirs, and a detector 4 for detecting the presence of analyte at some point along the length of the column. Both the sample and separation buffer reservoirs are connected (for example by electrodes 5) electrically to a voltage control device (not shown). Also included in the apparatus is a means 6 for controlling the variable bulk flow velocity through the separation column. For example, a regulated pressure control device could be connected to either the sample reservoir or separation buffer reservoir. The pressure differential across the sample and separation buffer ends of the separation column (and, hence, the bulk flow rate) can be made to vary with time, either linearly, or non-linearly (e.g., exponentially or step-wise) throughout the electrophoretic separation.

Incorporation of leading electrolytes (LE) into the separation buffer leads to isotachophoretic concentration and separation of analytes. By changing the bulk flow velocity over time during the separation, analytes are sequentially eluted onto the separation column from the sample vessel where they can individually be detected as resolved zones or peaks.

The primary advantage of this invention over prior art methods of electrophoresis is that it requires much shorter separation lengths and a much smaller total area or footprint on a microfluidic chip. The use of continuous sample introduction and variable bulk flow has the major advantage over conventional CE methods of not requiring any injection mechanism, eliminating the associated costs and footprints of such mechanisms. Consequently, much smaller chips can be used, reducing the cost of fabrication. Additionally, reduction of the area required for electrophoretic separation allows for the integration of more analysis elements (sample preparation, chemical reaction, etc.) into a fixed chip area.

Prior art electrophoresis methods have generally employed a constant bulk flow during the separation, either arising solely from native EOF or through the use of controlling mechanisms. A modified constant bulk flow, such as a pressure induced flow counter to EOF, can be used to provide increased resolution for a separation of two closely migrating analytes or increasing the time to allow analytes to reach the elevated concentration dictated by the Kohlrausch regulating function under ITP conditions. However, it is of limited utility for separations involving more than two analytes. For example, if three analytes of interest are present, a constant counter bulk flow can be set to provide enhanced resolution and enrichment of the first two analytes; however the third analyte will then likely move through the column in the opposite direction, away from the detector. In a defined injection electrophoretic method as is commonly practiced, the third analyte peak would likely migrate out of the column and never be detected. This can be disastrous for ITP separations where the third analyte could be the TE, as the TE provides the trailing boundary for the next slowest analyte. On the other hand, if the constant bulk flow is chosen so that the third analyte does migrate in the correct direction towards the detector, the desired resolution may not be achieved between the first two analytes.

According to one embodiment of the present invention, the separation buffer contains a LE and the bulk flow is set in the direction from the separation buffer reservoir to the sample reservoir. The magnitude of the bulk flow is initially high enough to allow LE to flow through the separation column and into the sample reservoir. Consequently, the ITP process occurs outside of the separation column on an ionic boundary defined by the diffusion and dispersion of the LE into the sample matrix. The bulk flow is varied over time during the separation in a systematic way to provide the desired enrichment and elution of all analytes onto the column. In the three-analyte example, the bulk flow would be varied so that early in the separation, it would provide the desired resolution and enrichment of the first two analytes, and then later in the separation it would provide the desired resolution and enrichment between the second and third analytes.

Even for separations of just two analytes, the method of the current invention has advantages over prior art electrophoretic methods employing constant bulk flow. With a constant bulk flow, in order to achieve a desired resolution between two closely migrating analytes requires accurate and precise control of the value of the bulk flow velocity. In many situations (because of variation of the electroosmotic flow, for example), it is difficult or impossible to control a fixed bulk flow velocity to the required accuracy and precision; this difficulty is exacerbated when using surface modifications to control EOF, which can be irreproducible in production and can degrade over time within a given column. With the current invention, the desired resolution is set by the choice of the rate of change of the bulk flow velocity, or the bulk flow acceleration. Because column-to-column or run-to-run variations in the electroosmotic mobility do not effect the bulk flow acceleration, it is easier to set the acceleration with the necessary level of precision.

The method of varying the hydrodynamic flow while providing continuous sample introduction used according to the present invention is based upon balancing electrophoretic velocities and bulk fluid velocity in order to discriminate different constituents within a mixture. Typically, the analyte electrophoretic velocities and the bulk velocity are in opposite directions in the separation column in order to increase species' resolutions. The magnitude of the bulk flow velocity is initially greater than the magnitude of the electrophoretic velocity of any of the analyte species, and analyte is therefore excluded from entering the column. The bulk flow is then decreased while electrophoresis remains constant. When the magnitude of the bulk flow velocity becomes less than the magnitude of the electrophoretic velocity of an analyte, that analyte will enter the column and migrate towards the detector. As the analyte moves past the detector it will be detected as a step or moving boundary. Analytes with different electrophoretic mobilities will be resolved because they will enter the column at different times (as the bulk velocity is decreased) and because, once in the column, they will migrate towards the detector at different speeds. Because different analytes are made to enter the capillary at different times, very short separation columns can be used to produce high-resolution separations. The method of varying the hydrodynamic flow while providing continuous sample introduction referred to herein as gradient elution moving boundary electrophoresis (GEMBE). The GEMBE method is also described in J. G. Shackman, M. S. Munson, and D. Ross, *Analytical Chemistry* volume 79, pp. 565-571 (2007), which is hereby incorporated by reference.

Figure 2A:
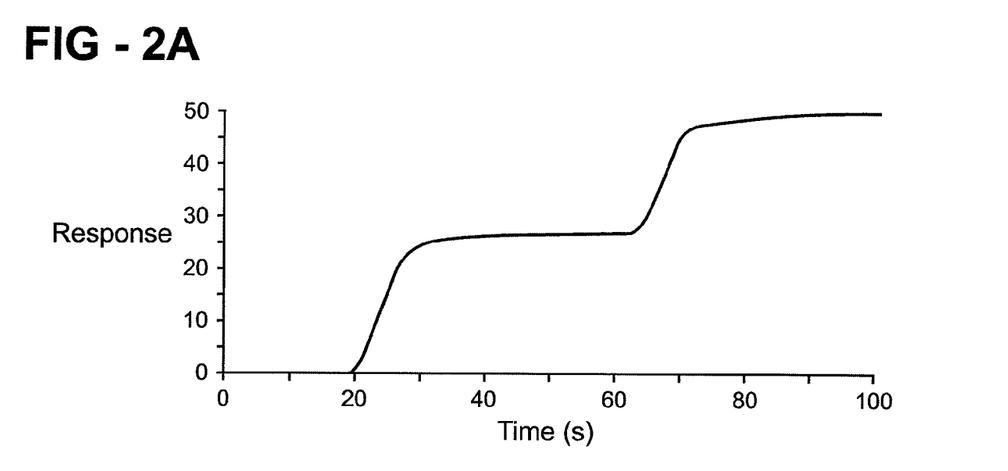
FIG. 2a is a graph of detector response with respect to time for the separation of two similar dyes using a GEMBE apparatus at different rates of bulk flow rate acceleration.
Figure 2B:
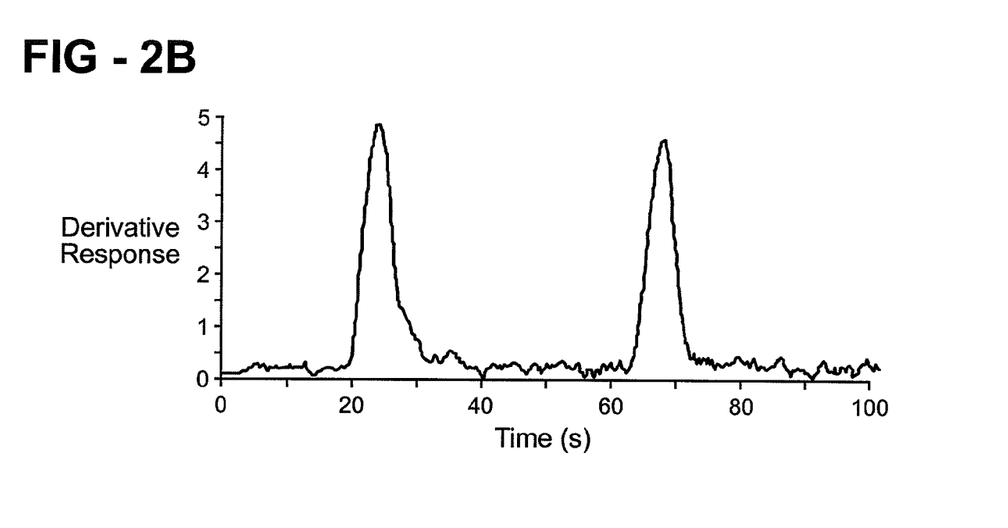
FIG. 2b is a graph of the derivative of detector response with respect to time for the separation of two similar dyes using a GEMBE apparatus at different rates of bulk flow rate acceleration.
Figure 3A:
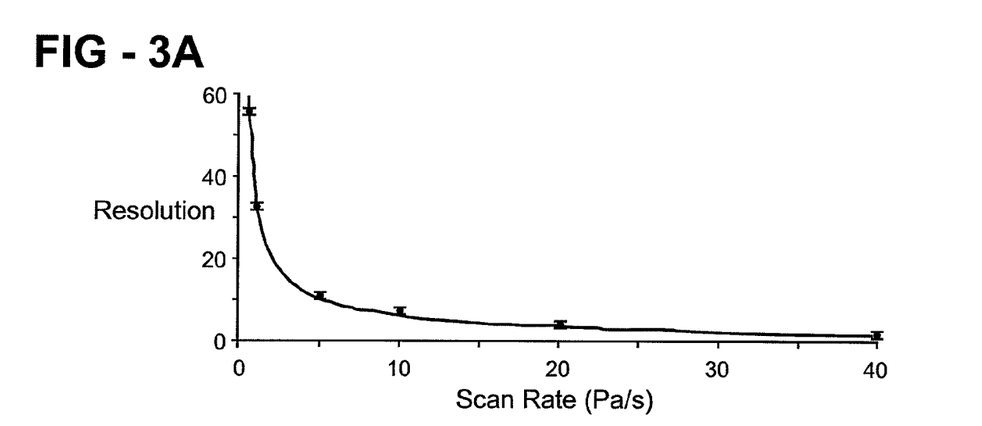
FIG. 3a is a graph that depicts the effect of pressure sweep rates (or bulk flow acceleration) on the resolution between analytes in a GEMBE separation.
Figure 3B:
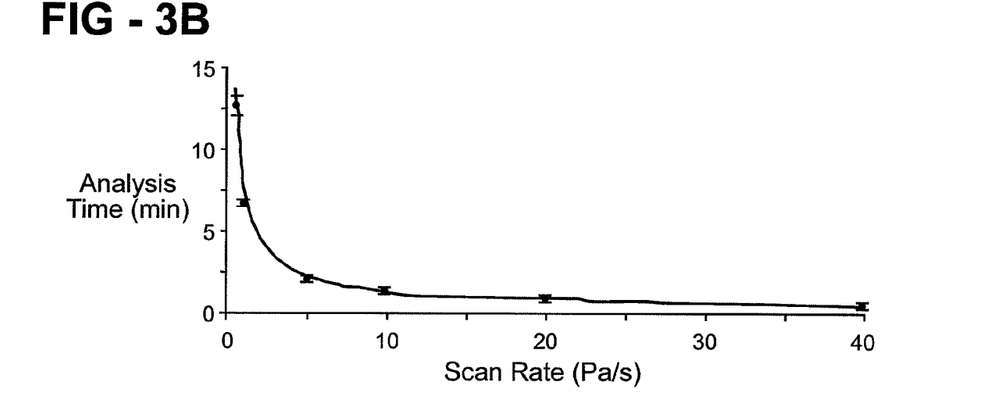
FIG. 3b is a graph that depicts the relationship between total analysis time and pressure sweep (or scan) rate.
Figure 3C:
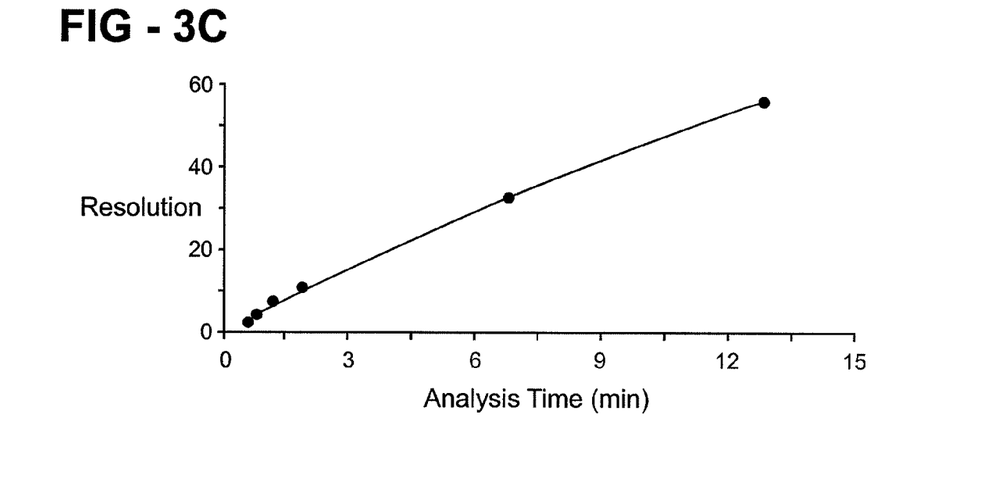
FIG. 3c is a graph that depicts the relationship between resolution and total analysis time.

The resolution of the separation can be increased by reducing the rate at which the bulk velocity is decreased (the bulk flow acceleration) in order to increase the time between the points at which each analyte enters the capillary. According to one working example, two similar fluorescent dyes, fluorescein and carboxyfluorescein were separated in a GEMBE apparatus at different rates of bulk flow acceleration. The apparatus used was similar to that depicted in FIG. 4. The separation column was a 3 cm length capillary with an inner diameter of 30 µm and an outer diameter of 360 µm. The inlet end of the capillary was connected via a 360 µm i.d. hole to a 150 µL volume sample reservoir. The outlet end of the capillary was connected via a silicone septum to a sealed, pressure-controlled waste reservoir. A sample solution containing 1 µmol/L each of fluorescein and carboxyfluorescein in 0.5 mol/L tris-borate buffer (0.5 mol/L tris(hydroxymethyl)aminomethane and 0.5 mol/L boric acid) was placed in the sample reservoir and the waste reservoir and capillary were filled with blank (containing no fluorescein or carboxyfluorescein) 0.5 mol/L tris-borate buffer. A voltage of −3000 V was applied to the sample reservoir, while the waste reservoir was electrically grounded. During the separation, the bulk flow was a combination of electroosmotic flow resulting from the applied voltage and pressure-driven flow resulting from the applied pressure at the waste reservoir. The bulk flow velocity was varied by changing the pressure applied to the waste reservoir. Detection of the analytes was performed at a distance of 1 cm from the sample inlet using a fluorescence microscope and color CCD camera. The applied pressure at the start of the separation was made great enough to exclude both analytes from entering the separation capillary, e.g., on the order of about 1000 Pa. The pressure was then swept at a fixed rate (so as to produce a fixed bulk flow acceleration) to sequentially introduce the analytes, generally on the order of 1 Pa/s. The detector response produced a stepwise pattern, similar to that depicted in FIG. 2a. The derivative of the detector response with respect to time showed a pattern of peaks similar to a conventional electropherogram, as depicted in FIG. 2b. FIG. 3a depicts the effect of different pressure sweep rates (or bulk flow acceleration rates) on the resolution between the analytes in a GEMBE separation while FIG. 3b shows the relationship between resolution and total analysis time. The separations were performed with the detector only 1 cm from the capillary inlet.

Figure 4:
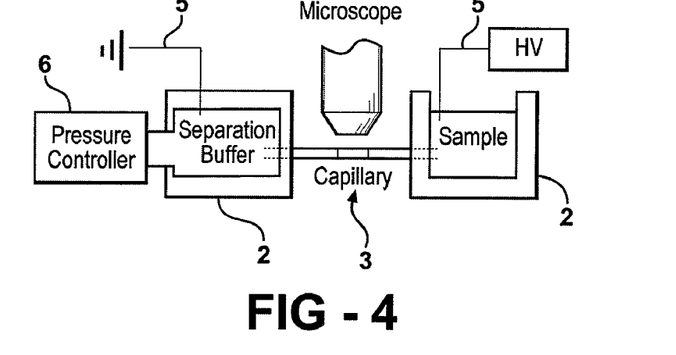
FIG. 4 is a schematic drawing of a capillary system that can be used according to another embodiment of the present invention.
Figure 6A:
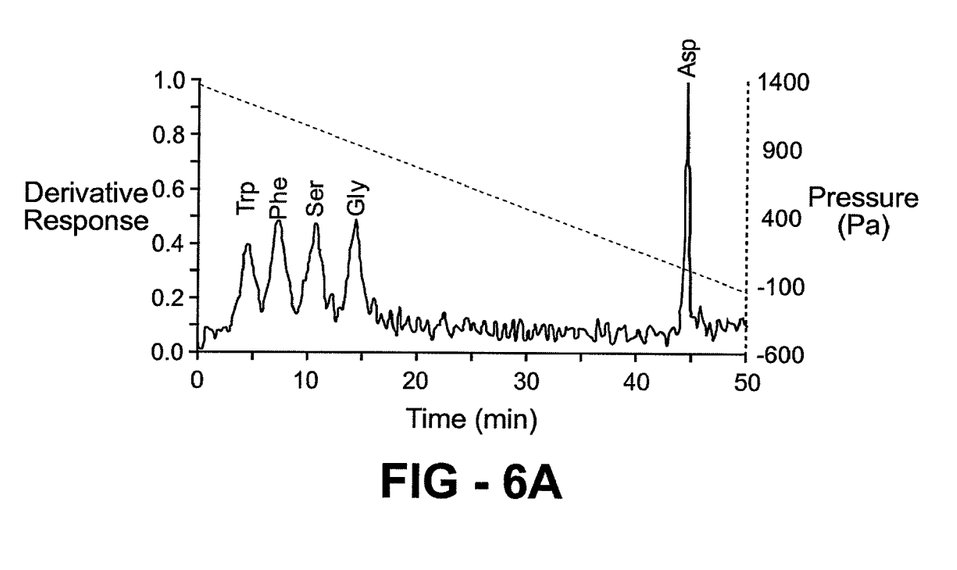
FIG. 6a shows the results of a linear pressure sweep (constant bulk flow acceleration) for a GEMBE separation of amino acids.
Figure 6B:
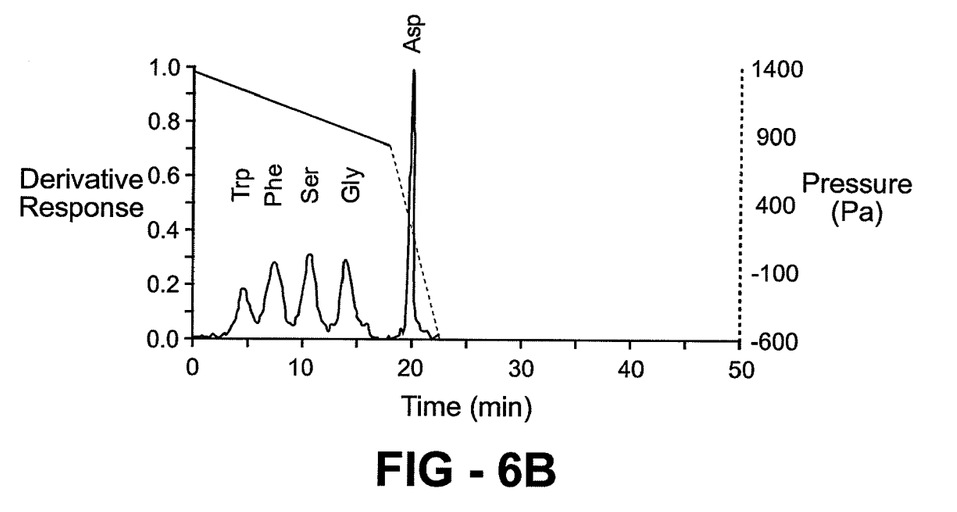
FIG. 6b shows the results of a two-step gradient for a GEMBE separation of amino acids.

As an alternative to increasing resolution between species, the analysis time of a separation can be shortened in instances when more than sufficient resolution is obtained with conventional electrophoresis, leading to faster analysis times and higher throughput. According to another working example, the effect of decreasing analysis time is shown in FIG. 4, wherein five amino acids are separated by GEMBE. In this example, five fluorescent dansyl-labeled amino acids (tryptophan, phenylalanine, serine, glycine, and aspartic acid) in 0.5 mol/L Tris borate buffer were placed in the sample reservoir at equal concentrations of 1 mmol/L. Other experimental conditions were the same as the example above. FIG. 6a shows the results of a linear pressure sweep (constant bulk flow acceleration), while FIG. 6b shows the results of a two-step gradient to elute the four fastest migrating amino acids at one sweep rate, followed by a faster rate to elute the slowest amino acid, aspartic acid.

With GEMBE, the analyst is afforded all the experimental parameters available to traditional capillary electrophoresis separations; including electric field strength separation column dimensions, temperature, background electrolyte composition, etc., as well as the new parameters of bulk flow velocity and acceleration. All these parameters can be adjusted to realize a separation of analytes. For a given separation column and background electrolyte, the voltage range can be determined through the use of Ohm's Law plots, which present the relationship between observed current and applied voltage. Positive deviations from linearity at higher voltages indicate Joule heating of the capillary, which can degrade the separation, and establish an upper voltage limit (along with physical limitations of available voltage sources). Common field strengths are between 100 and 1000 V cm$^{-1}$. As with conventional CE, temperature control of the separation column can be utilized to extend the working voltage range, especially in the cases of highly conductive solutions. Either polarity of applied voltage can be used, so that the direction of electrophoretic migration of the analytes can be from inlet to outlet or from outlet to inlet. The magnitude and direction of bulk flow would then be set accordingly so that during the separation the analytes would move from the inlet to the outlet.

Separation column cross sectional areas are typically less than 0.1 mm$^2$ in order to allow rapid heat transfer and prevent Joule heating of the capillary. The lower limit of cross sectional area is dictated both by availability of substrate and, when using pressure to control the bulk fluid flow, the limitation of the pressure control device to affect bulk flow against high back pressures. Commonly 100 to 20000 µm$^2$ cross sectional areas can be used with good effect. One of the many benefits of GEMBE is the ability to use short separation columns. Separation lengths are typically limited by geometrical constraints including electrical and/or hydrodynamic connections to the apparatus—as well as having available room for detection instruments. Using a standard fluorescent microscope as a detector, column lengths on the order of 1 cm can be utilized without great difficulty.

As in prior art electrophoretic methods, it is also possible to use this method in conjunction with additives to modify the electrophoretic mobility of analytes and provide different separation selectivity. Examples of additives include cyclodextrins or other chiral selectors for chiral separations, micelles, micro emulsions, liposomes, dendrimers or other additives that act as a pseudostationary phase to provide selectivity based upon the strength of interaction between the additives and the analytes. Note that with appropriate additives, this method can be used to separate neutral molecules.

The steps typically required to implement the GEMBE method of the present invention include:

1) providing a reservoir (the separation buffer reservoir) of solvent or solution (the separation buffer) in fluid contact with the outlet end of a separation column;

2) filling the separation column with the solvent or solution;

3) introducing a sample solution to the inlet end of the separation column;

4) producing a bulk flow of the solvent or solution through the separation column;

5) applying a voltage along the length of the separation column to produce an electric field to drive the electrophoretic motion of analyte(s) through the column; and 6) changing the bulk flow velocity over time, so that each of the analytes of interest will sequentially be eluted from the sample solution into the column.

A possible additional step is to detect the analytes as they move through the column. A plot of detector signal vs. time will have steps similar to the result of prior art moving boundary electrophoresis methods. Each step will correspond to an analyte, and the height of each step will correspond to the concentration of that analyte in the sample. Any detector usable with prior art electrophoresis methods could be used.

The solvent or solution used in step 1 can be any solvent or solution useable for electrophoretic separations: aqueous or non-aqueous buffer, with or without a pseudostationary phase or other additives.

Examples of appropriate separation columns include capillaries or micro channels, made from glass or polymer materials or any other electrically insulating materials. The cross-sectional size of the inside of the columns would typically be less than 0.1 mm$^2$, but could be larger as in prior art of tubular free zone electrophoresis. The column could also contain a stationary phase, present either as a packed bed or wall coating or any other form used for capillary electrochromatography.

The sample solution of step 3 can be prepared in a solvent or buffer that is similar or dissimilar to the solvent or buffer of step 1. The types of analytes that can be separated include any analytes that can be separated by conventional CE methods (small molecules (molecular weight<1000 g/mol), large molecules (molecular weight>1000 g/mol), particles, amino acids, nucleic acids, carbohydrates, proteins, peptides, pesticides, pharmaceuticals, cells, viruses, bacteria, nanoparticles, etc.)

The bulk flow of step 4 can be driven either by electroosmosis (using the same applied voltage as step 5) or by applied pressure gradients or both. The direction of the bulk flow can be in either direction through the column, from inlet to outlet or from outlet to inlet. The terms 'inlet' and 'outlet' refer to the net direction of motion of the analyte molecules. During a separation, analytes move from the sample solution through the column inlet, traverse the column length, and exit the column through the column outlet.

The sign of the applied voltage depends on the direction of bulk flow and the sign of the charge of the analyte molecules. For example, if the analyte molecules are negatively charged in solution (or if they partition into a negatively charged pseudostationary phase) and the bulk flow is from outlet to inlet, then the voltage applied to the inlet will be negative relative to the voltage applied to the outlet. In most cases, when the desired result is high resolution in a short column, the bulk flow of the solvent and the electrophoretic motion of the analytes should be in opposite directions. However, in cases where the resolution is more than adequate, the analysis time can be reduced by using a bulk flow that is in the same direction as the electrophoretic motion.

The bulk flow is initially set so that all or nearly all of the analytes of interest do not enter the column. During the separation, the bulk flow is changed (in step 6) over time so that each of the analytes of interest will sequentially move into the column. There are different ways that the bulk flow rate could be varied over time. The bulk flow can be driven by a combination of electroosmosis and externally applied pressure difference between the column inlet and outlet. The applied pressure is varied over time to vary the bulk flow rate. The bulk flow could also be driven entirely by electroosmosis and the electroosmotic mobility could be varied over time to vary the bulk flow rate. One example of this would be the use of a voltage applied across the walls of the separation column. Most typically, the bulk flow velocity will be varied in a smooth, continuous fashion over the course of a separation.

According to another embodiment, the present invention is directed to a method that involves performing GEMBE under ITP conditions. As discussed above, GEMBE is a continuous injection method of electrophoresis combined with a variable bulk flow. In GEMBE, the counter flow, which has EOF as the dominant component, is manipulated by controlling the pressure applied to the ends of the separation channel or capillary. The counter flow is initially great enough to exclude analytes from entering the separation column; as the bulk fluid flow is decreased from high to low rates, analytes are sequentially eluted onto the column and detected as boundary interfaces. GEMBE exhibits the advantages of short separation lengths (typically 1 cm or less) and simplicity of design because there is no need to form an injection plug, making it highly amenable to high throughput and high density microdevices.

By introducing LE into a GEMBE separation buffer and TE into the sample matrix, a novel form of ITP has been developed which is referred herein as gradient elution ITP (GEITP). The GEITP method is also described in J. G. Shackman and D. Ross, *Analytical Chemistry* volume 79, pp. 6641-6649 (2007), which is hereby incorporated by reference. As opposed to conventional ITP methods, GEITP enrichment occurs outside of the separation column at a counter flow rate great enough to push LE into the sample reservoir, forming an ionic interface near the column inlet. When the voltage is applied, analyte ions are focused by ITP on the ionic interface. Similar to GEMBE, as the counter flow rate is reduced, the enriched plug of analyte is introduced onto the column. Unlike GEMBE, however, the analytes to be separated are focused into peaks before they enter the separation column, so that the detector response produces a pattern of peaks rather than steps. Consequently, there is no need to take the derivative of the detector response to produce a peak pattern similar to a conventional electropherogram. GEITP allows for high analyte concentration enhancement and high resolution separations in short lengths, involves only a single microcolumn, and does not require a discrete injection method, which will aid in transfer to microdevices. Additionally, as compared to other ITP methods, GEITP does not necessitate any buffer or polarity switching, yielding a more reliable and automatable system.

An additional advantage of GEITP over other non-ITP methods for sample enrichment (sample stacking, temperature gradient focusing, for example) is that it is relatively insensitive to the presence of salts or other ionic impurities in the sample matrix. Such ionic impurities act as additional spacer electrolytes in the sample, improving the resolution of analytes of interest.

Figure 5A:
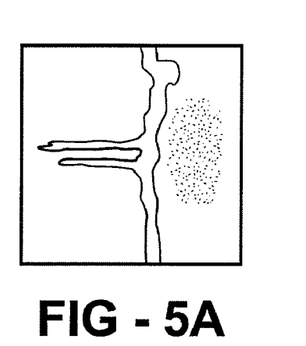
FIGS. 5a-5d are images of dye separations using the apparatus of FIG. 4.
Figure 5B:
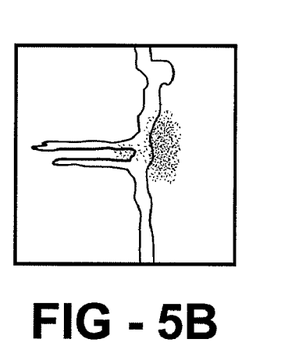
Figure 5C:
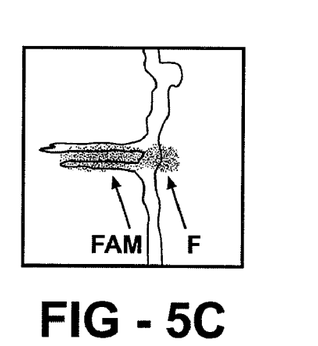
Figure 5D:
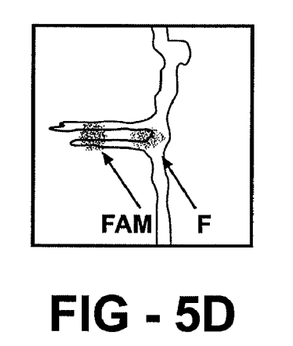
Figure 5E:
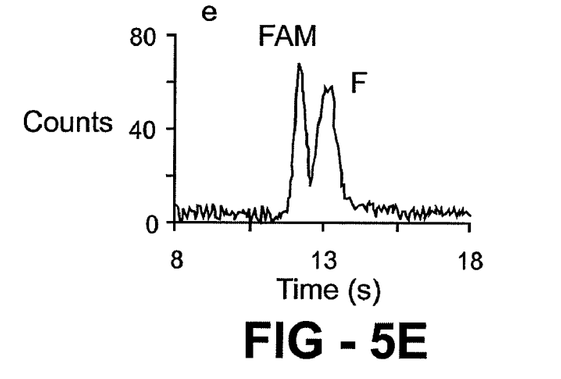
FIG. 5e is a graph of detector response with respect to time for the separation of two similar dyes using the GEITP method with the point of detection located just 30 μm from the capillary inlet.

According to another working example that illustrates the short lengths required for GEITP separations, fluorescein and carboxyfluorescein were enriched and separated in a GEITP apparatus similar to the one shown in FIG. 4. The separation column 3 was a 3 cm length capillary with an inner diameter of 30 μm and an outer diameter of 360 μm. The inlet end of the capillary was connected via a 360 μm i.d. hole to a 150 μL volume sample reservoir 1. The outlet end of the capillary was connected via a silicone septum to a sealed, pressure-controlled separation buffer reservoir 2. A sample solution containing fluorescein, carboxyfluorescein, 1 mol/L glycine spacer and 0.5 mol/L tris-borate buffer was placed in the sample reservoir. A leading electrolyte solution of 100 mmol/L citric acid balanced to pH 8.3 with tris(hydroxymethyl)aminomethane (tris) was placed in the separation buffer reservoir. A negative voltage (1800 V) was applied to the sample reservoir via electrode 5 while the separation buffer reservoir containing LE electrolyte and tris counter ion was electrically grounded via electrode 5. During the separation, the bulk flow was comprised of a combination of electroosmotic flow resulting from the applied voltage and pressure-driven flow resulting from the applied pressure at the separation buffer reservoir. The bulk flow velocity was varied by changing the pressure applied to the separation buffer reservoir. The GEITP process can be visualized in FIGS. 5a-5d. The images of FIGS. 5a-5d were taken using a fluorescence microscope and color CCD camera through the sample reservoir at the capillary inlet, where the polyimide coating was removed. In this instance, citrate acted as the LE and borate as the TE, although other systems utilizing chloride or acetate as LE were also successfully used (data not shown). At high counter flow rates (1800 Pa applied pressure; FIG. 5a) no enrichment was detectable, likely due to the high rate of LE efflux and rapid dispersion. As the counter flow rate was reduced (850 Pa; FIG. 5b), a single concentrated fluorescent spot outside of the capillary was observed. When the flow rate was further reduced (730 Pa; FIG. 5c), FAM was introduced onto the capillary. Note that the use of the spacer excluded fluorescein from entering the capillary until further reduction in counter flow (590 Pa; FIG. 5d). Although not optimal in the capillary format, with detection through the sample reservoir, extremely short separations can be realized using GEITP, with separation of FAM and fluorescein within 30 μm. FIG. 5e shows the detector response with the detection point set at a distance of 30 μm from the capillary inlet. For this separation the sample solution and separation buffer were as described above for FIGS. 5a-d. The applied pressure was initially set to 850 Pa, and was varied at a rate of −10 Pa/s.

The concentration enrichment of analytes will be affected by several variables, including initial bulk flow rate, applied electric field strength, LE concentration, and the acceleration of the bulk flow (or change in bulk flow velocity). As an example, carboxyfluorescein was enriched while individually varying the above parameters, each of which had a significant affect upon enrichment. Upon optimization of the ITP enrichment process, roughly 100000-fold improvements in limits of detection were observed in 2 minutes.

When spacer electrolytes are used, in addition to improving enrichment, the resolution of the separation can be increased by reducing the rate at which the bulk velocity is decreased (the bulk flow acceleration) in order to increase the time between the points at which each analyte enters the capillary. As an example, two similar fluorescent dyes, fluorescein and carboxyfluorescein were separated using glycine as a spacer under various bulk flow accelerations. For slower bulk flow acceleration, the analytes and the spacer have a longer time to focus so more analyte and spacer molecules are focused at the interface of the LE and TE. Trace analytes will remain at a concentration much lower than the LE concentration and so will focus into Gaussian peaks. The spacer electrolyte, on the other hand, will rapidly focus to the maximum concentration as determined by the Kohlrausch regulating function, after which point any further addition of spacer to the focused band will result in an increased width of the band, and thus an increased amount of space between the analyte peaks.

Figure 8A:
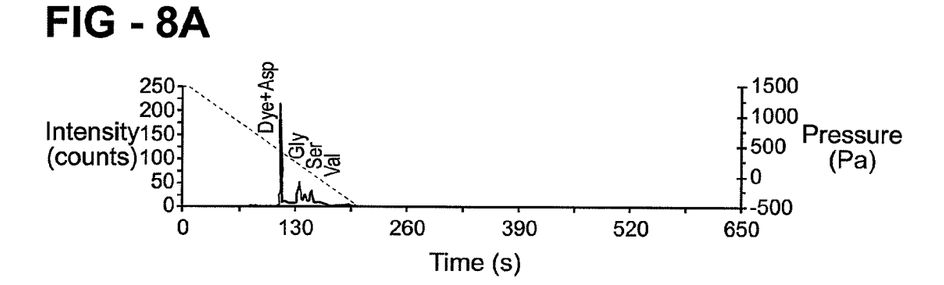
FIG. 8a is a graph of detector response with respect to time for the separation of amino acids using the GEITP method and a constant, relatively rapid pressure sweep rate.
Figure 8B:
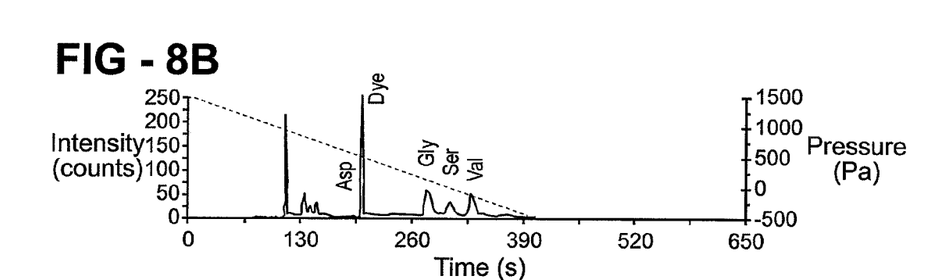
FIG. 8b is a graph of detector response with respect to time for the separation of amino acids using the GEITP method and a constant, but slower pressure sweep rate.
Figure 8C:
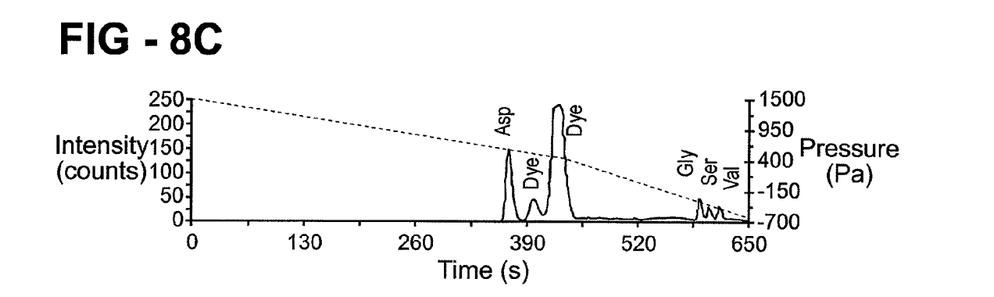
FIG. 8c is a graph of detector response with respect to time for the separation of amino acids using the GEITP method and a non-constant pressure sweep rate.

In addition to using a single discreet spacer to provide resolution between two analytes, a mixture of spacer electrolytes can be used to provide resolution between multiple analytes. If the spacer mixture contains a sufficiently large number of different electrolyte species, it can act as a continuous spacer that provides resolution over a broad, continuous range of electrophoretic mobilities. The ampholyte mixtures employed for isoelectric focusing have been used in this way with conventional ITP. In another example described here, they were used for the GEITP separation of a mixture of amino acids in an apparatus similar to the one shown in FIG. 4. The separation column 3 was a 3 cm length capillary with an inner diameter of 30 μm and an outer diameter of 360 μm. The inlet end of the capillary was connected via a 360 μm i.d. hole to a 150 μL volume sample reservoir 1. The outlet end of the capillary was connected via a silicone septum to a sealed, pressure-controlled separation buffer reservoir 2. A sample solution containing a mixture of carboxyfluorescein-labeled amino acids (aspartic acid, glycine, serine, and valine), 5% (v/v) ampholyte mixture (high-resolution ampholyte mixture (pH 3.0-10.0) from Sigma-Aldrich Co.) and 0.5 mol/L tris-borate buffer was placed in the sample reservoir. A leading electrolyte solution of 50 mmol/L citric acid balanced to pH 8.3 with tris(hydroxymethyl)aminomethane (tris) was placed in the separation buffer reservoir. A negative voltage (2700 V) was applied to the sample reservoir via electrode 5 while the separation buffer reservoir containing LE electrolyte and tris counter ion was electrically grounded via electrode 5. During the separation, the bulk flow was comprised of a combination of electroosmotic flow resulting from the applied voltage and pressure-driven flow resulting from the applied pressure at the separation buffer reservoir. The bulk flow velocity was varied by changing the pressure applied to the separation buffer reservoir. FIG. 8(a-c) shows the detector response (solid curves) with the detection point set at a distance of 1 cm from the capillary inlet. The applied pressure for each separation is also shown in FIG. 8(a-c) as the dashed curves. Under modest acceleration conditions (−10 Pa/s), glycine, serine, and valine are nearly baseline resolved while aspartic acid and the free dye comigrate (FIG. 8a). Reducing the acceleration by half yielded baseline resolution of the slow analytes and partial resolution of aspartic acid from the free dye (FIG. 8b). Utilizing a two-stage gradient (FIG. 8c), baseline resolution of all components could be achieved in ~10 min.

The steps typically required to implement a GEITP separation according to the present invention include:

1) providing a reservoir (the separation buffer reservoir) of solvent or solution (the separation buffer) in fluid contact with the outlet end of the separation column;

2) introducing a leading electrolyte into the separation buffer that exhibits an electrophoretic mobility higher than that of the analyte(s) present in the sample 3) filling the separation column with the separation buffer;

4) introducing a sample solution to the inlet end of the separation column;

5) (optional) introducing a terminating electrolyte into the sample solution that exhibits an electrophoretic mobility smaller than that of the analyte(s) present in the sample 5a) introducing one or more spacing electrolytes to the sample solution to provide non-detectable zones to differentiate the detectable analyte zones.

6) producing a bulk flow of the separation buffer through the separation column in a direction from the separation buffer reservoir to the sample reservoir;

7) applying a voltage between the ends of the separation column to produce an electric field to drive the electrophoretic motion of analyte(s) from the sample towards the junction of the sample reservoir and the separation column;

8) changing the bulk flow velocity over time, so that each of the analyte(s) of interest will sequentially be concentrated on the boundary between the leading electrolyte and the sample (or terminating) electrolyte and eluted from the sample solution into the column; and 9) detecting the analyte(s) as they sequentially traverse the column The separation buffer used in step 1 can be any solvent or solution useable for electrophoretic separations, including an aqueous or non-aqueous buffer, with or without a pseudostationary phase or other additives.

Examples of appropriate separation columns would be capillaries or microchannels, made from glass or polymer or any other electrically insulating material. The cross-sectional size of the inside of the column would typically be less than $0.1 \text{ mm}^2$, but could be larger as in prior art of tubular free zone electrophoresis. The column could also contain a stationary phase, present either as a packed bed or wall coating or any other form used for capillary electrochromatography.

The sample solution of step 4 can be prepared in a solvent or buffer that is similar or dissimilar to the separation buffer of step 1. However, it must differ from the separation buffer in the type or concentration of electrolytes. Specifically, the separation buffer must contain a higher concentration of the leading electrolyte. The types of analytes that can be separated include any analytes that can be separated by conventional CE methods (small molecules, large molecules, particles, amino acids, nucleic acids, carbohydrates, proteins, peptides, pesticides, pharmaceuticals, cells, viruses, bacteria, etc.)

The bulk flow of step 6 can be driven either by electroosmosis (using the same applied voltage as step 7) or by applied pressure gradients or both. The direction of the bulk flow can be in either direction through the column, from inlet to outlet or from outlet to inlet, though with the GEITP method the bulk flow is typically from outlet to inlet. The terms 'inlet' and 'outlet' refer to the net direction of motion of the analyte molecules. During a separation, analytes move from the sample solution through the column inlet, traverse the column length, and exit the column through the column outlet.

The sign of the applied voltage depends on the direction of bulk flow and the sign of the charge of the analyte molecules. For example, if the analyte molecules are negatively charged in solution (or if they partition into a negatively charged pseudostationary phase) and the bulk flow is from outlet to inlet, then the voltage applied to the inlet will be negative relative to the voltage applied to the outlet.

The bulk flow is initially set so that all of the analytes of interest do not enter the column while LE flows into the sample chamber. During the separation, the bulk flow is changed (in step 8) over time so that each of the analytes of interest will sequentially move into the column. As with GEMBE, the bulk flow rate is typically varied in a continuous manner during the course of the separation.

There are different ways that the bulk flow rate could be varied over time. The bulk flow can be driven by a combination of electroosmosis and externally applied pressure difference between the column inlet and outlet. The applied pressure can varied over time to vary the bulk flow rate.

The bulk flow could also be driven entirely by electroosmosis and the electroosmotic mobility could be varied over time to vary the bulk flow rate. One example of this would be the use of a voltage applied across the walls of the separation column.

For GEMBE and GEITP, Background electrolyte compositions are typically dependent upon the analytes of interest, and are most commonly conductive aqueous buffered ionic solutions. The background electrolyte pH and ionic strength are two primary factors in modifying electroosmotic flow and realizing separation of two distinct analytes. Additionally, additives, such as organic modifiers or polymers, can be used to enhance selectivity. A buffer usually will have a pKa at or near the desired working pH and usually will be less than 250 mmol/L or less than 100 mmol/L in order to avoid excessive conductivity. An additional constraint for performing GEITP separations are that the LE in the separation buffer solution has an electrophoretic mobility higher than that of the fastest analyte of interest, although an excessively large difference will only increase the time needed to perform the analyses; furthermore, the TE present in the sample matrix must have a mobility less than that of the slowest analyte.

Figure 7:
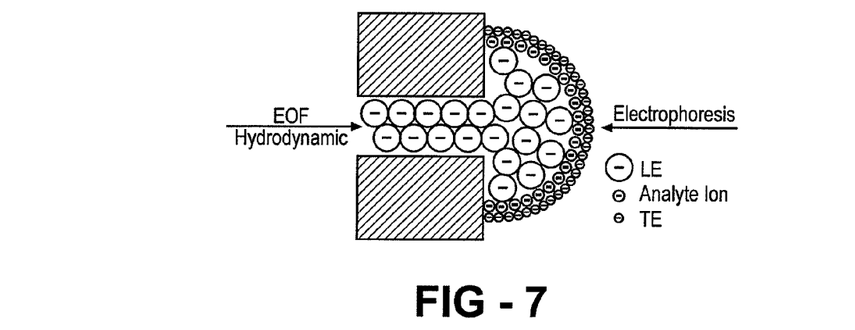
FIG. 7 is a schematic of the formation of the LE-TE interface outside the separation column inlet, and focusing of analyte at that interface.

When using an applied pressure to control the bulk flow rate, the initial pressure is typically chosen to exclude entrance of any detectable analytes onto the separation column and, in the case of GEITP, high enough to force LE into the sample reservoir, as shown schematically in FIG. 7. In a standard linear method (constant bulk flow acceleration), the pressure is decreased in a linear fashion until all analytes have entered the column for detection. The pressure sweep rate (acceleration) can be reduced in order to increase the resolution of analytes or increased in order to decrease analysis time. Generally 0.1 Pals to 10 Pa/s rates can be utilized on a standard pressure control system (whether gravity, gas, piston driven, etc.) with the other separation parameters similar to that described above. Alternatively, the pressure can be held constant, stepped, or varied in other non-linear manners through portions of the separation.

It should be noted that the GEMBE method can be used for the separation of both anionic and cationic species in the same separation with analysis times greatly reduced as compared to conventional methods. For example, if a negative voltage is applied to the inlet end of the separation column, anions will electrophoretically migrate from the inlet to the outlet, and cations will electrophoretically migrate from the outlet to the inlet. The bulk flow velocity will initially be set in the direction from outlet to inlet and at a magnitude that is greater than the electrophoretic migration speed of the anionic analytes. As the bulk flow velocity is reduced each of the anionic analytes will be eluted into the column and detected as above. The bulk flow velocity would then be varied further until it changes direction (from inlet to outlet). The magnitude of the bulk velocity would then increase with time, and each cationic analyte would be pulled into the column when its electrophoretic velocity is overcome by the increasing bulk flow velocity. Further, it is noted that the GEITP method of the present invention can be used for the enrichment and separation of analytes with a wide range of mobilities, so long as the chosen LE and TE electrophoretic mobilities bound the mobilities of the analytes of interest. Example molecules include small dyes, amino acids, proteins, and DNA.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above.

What is claimed is:

1. A method for performing electrophoretic separation from a sample of one or more compounds having distinct electrophoretic mobilities, comprising the steps of:
   a) providing a separation path, the separation path having an inlet end and an outlet end;
   b) providing a separation buffer in fluid contact with said outlet end;
   c) providing a sample in fluid contact with said inlet end of the separation path, the sample containing one or more compounds having distinct electrophoretic mobilities;
   d) applying an electric field along the length of the separation path to drive electrokinetic motion of the compounds;
   e) varying with respect to time a bulk fluid flow through the separation path concurrent with the application of the electric field in order to affect whether and when each of the one or more compounds moves into and through the separation path, whereby, when the sample comprises multiple compounds with distinct electrophoretic mobilities, each such compound that moves into the separation path is made to do so at a different time; and
   wherein the sample is in fluid contact with the inlet end of said separation path continuously throughout the electrophoretic separation of the one or more compounds.

2. A method for performing electrophoretic separation of compounds according to claim 1, wherein a leading electrolyte is provided in the separation buffer and whereby the one or more distinct compounds are concentrated.

3. A method for performing electrophoretic separation of compounds according to claim 2, wherein a terminating electrolyte is provided in the sample.

4. A method for performing electrophoretic separation of compounds according to claim 2, wherein one or more spacing electrolytes are provided in the sample.

5. A method for performing electrophoretic separation of compounds according to claim 1, wherein the bulk fluid flow is comprised of at least one of electroosmotic flow and pressure-driven flow.

6. A method for performing electrophoretic separation of compounds according to claim 1, wherein the one or more distinct compounds are selected from the group consisting of small molecules, large molecules, particles, amino acids, nucleic acids, carbohydrates, proteins, peptides, pesticides, pharmaceuticals, cells, viruses, bacteria, and nanoparticles.

7. A method for performing electrophoretic separation of compounds according to claim 1, wherein the separation path is selected from the group consisting of a capillary tube, a micro fluidic channel, a micro fluidic channel on a microchip, and a separation column.

8. A method for performing electrophoretic separation of compounds according to claim 1, wherein an additive is provided in the separation path, which additive acts to modify the electrophoretic mobility of the one or more compounds in the sample.

9. A method for performing electrophoretic separation of compounds according to claim 1, further comprising the step of detecting each of the one or more compounds that moves into the separation path.

10. The method of claim 1, wherein said bulk fluid flow is varied with respect to time in a substantially continuous manner.

11. The method of claim 10, wherein said bulk fluid flow is varied linearly with substantially constant acceleration.

12. The method of claim 10 wherein said bulk fluid flow is varied non-linearly with non-constant acceleration.

13. The method of claim 10, wherein varying the bulk fluid flow through the separation path concurrent with the application of said electric field is the only step required to affect whether and when each of the one or more compounds moves into the separation path.

14. The method of claim 10, wherein a leading electrolyte is provided in the separation buffer, and whereby the one or more compounds are concentrated.

15. The method of claim 14, wherein one or more additional electrolytes are provided in the sample to act as isotachophoretic terminators or spacers.

16. The method of claim 15, wherein varying the bulk fluid flow through the separation path concurrent with the application of the electric field is the only step required to affect whether and when each of the one or more compounds moves into the separation path.

17. The method of claim 1, wherein varying the bulk fluid flow through said separation path concurrent with the application of the electric field is the only step required to sequentially introduce the two or more distinct compounds into the separation path.

18. A method for performing electrophoretic separation of one or more compounds having distinct electrophoretic mobilities, comprising the steps of:
   a) providing a separation path, the separation path having an inlet end and an outlet end;
   b) providing a separation buffer in fluid contact with said outlet end;
   c) providing a sample in fluid contact with the inlet end of the separation path, the sample containing one or more compounds having distinct electrophoretic mobilities;
   d) applying an electric field along the length of the separation path to drive electrokinetic motion of the compounds; and
   e) varying with respect to time and in a substantially continuous manner a bulk fluid flow through said separation path concurrent with the application of the electric field in order to affect whether and when each of the one or more compounds moves into the separation path, whereby, when the sample comprises multiple compounds with distinct electrophoretic mobilities, each such compound that moves into the separation path is made to do so at a different time.

19. The method of claim 18, wherein the bulk fluid flow is varied with respect to time linearly with substantially constant acceleration.

20. The method of claim 18, wherein the bulk fluid flow is varied with respect to time non-linearly with non-constant acceleration.

21. The method of claim 20, wherein varying the bulk fluid flow through the separation path concurrent with the application of the electric field is the only step required to affect whether and when each of the one or more compounds moves into the separation path.

22. The method of claim 18, wherein a leading electrolyte is provided in the separation buffer, and whereby the one or more compounds are concentrated.

23. The method of claim 22, wherein one or more additional electrolytes are provided in the sample to act as isotachophoretic terminators or spacers.

24. The method of claim 18, wherein varying the bulk fluid flow through the separation path concurrent with the application of the electric field is the only step required to affect whether and when each of the one or more compounds moves into the separation path.

* * * * *